United States Patent [19]

Noiles

[11] Patent Number: 4,801,301
[45] Date of Patent: * Jan. 31, 1989

[54] BALL AND SOCKET BEARING FOR ARTIFICIAL JOINT

[75] Inventor: Douglas G. Noiles, New Canaan, Conn.

[73] Assignee: Joint Medical Products Corporation, Stamford, Conn.

[*] Notice: The portion of the term of this patent subsequent to Feb. 10, 2004 has been disclaimed.

[21] Appl. No.: 942,298

[22] Filed: Dec. 16, 1986

Related U.S. Application Data

[63] Continuation of Ser. No. 473,431, Mar. 8, 1983, Pat. No. 4,642,123.

[51] Int. Cl.[4] ............................................. A61F 2/32
[52] U.S. Cl. ....................................... 623/23; 623/18
[58] Field of Search ................................... 623/16–23

[56] References Cited

U.S. PATENT DOCUMENTS

| | | | |
|---|---|---|---|
| 3,818,512 | 6/1974 | Shersher | 623/22 |
| 3,903,549 | 9/1975 | Deyerle | 623/22 |
| 4,004,300 | 1/1977 | English | 623/23 |

FOREIGN PATENT DOCUMENTS

| | | | |
|---|---|---|---|
| 65482 | 11/1982 | European Pat. Off. | |
| 7104212 | 5/1971 | Fed. Rep. of Germany. | |
| 2323456 | 11/1974 | Fed. Rep. of Germany | 623/22 |
| 2845231 | 5/1979 | Fed. Rep. of Germany | 623/18 |
| 2099259 | 3/1972 | France. | |
| 2416004 | 8/1979 | France | 623/22 |
| 2007980 | 5/1979 | United Kingdom. | |

OTHER PUBLICATIONS

Harris, William H., *Clinical Orthopaedics and Related Research*, No. 81, Nov.–Dec., 1971.
*Vitallium Harris Total Hip System*, Howmedica, Inc., Rutherford, N.J.
Pipino and Calderale, Acta Orthopaedica Belgica, vol. 46, pp. 5–13 (1980).
Pipino and Calderale, *Pan. Med.*, vol. 25, pp. 231–238 (1983).

Primary Examiner—Richard J. Apley
Assistant Examiner—David J. Isabella
Attorney, Agent, or Firm—Maurice M. Klee

[57] ABSTRACT

A ball and socket joint for implanting in the body is provided which comprises (1) a ball; (2) a cup to be affixed to bone which includes (a) a spherical cavity and (b) two coaxial pin members which extend into the cavity; and (3) a bearing member surrounding a portion of the ball and rotatable within said spherical cavity about said coaxial pin members, the bearing member having an asymmetric opening therein, the opening having an angular extent of less than 180° in at least one plane. In certain preferred embodiments, the cup includes first and second portions, the first portion to be affixed to bone, the second portion having associated therewith the coaxial pin members and being moveable with respect to the first portion to provide a plurality of possible orientations for the axis of rotation of the bearing member within the spherical cavity.

8 Claims, 4 Drawing Sheets

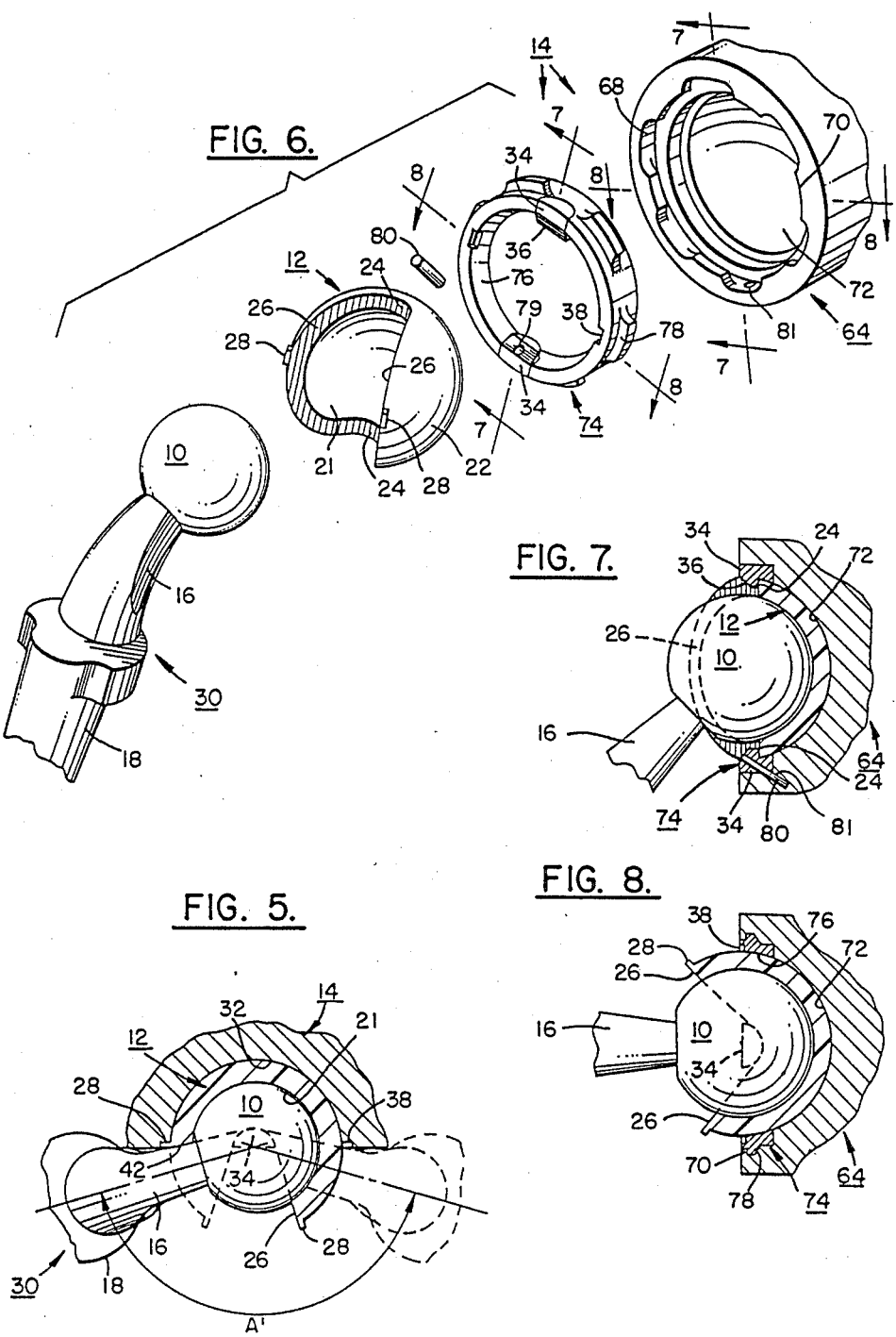

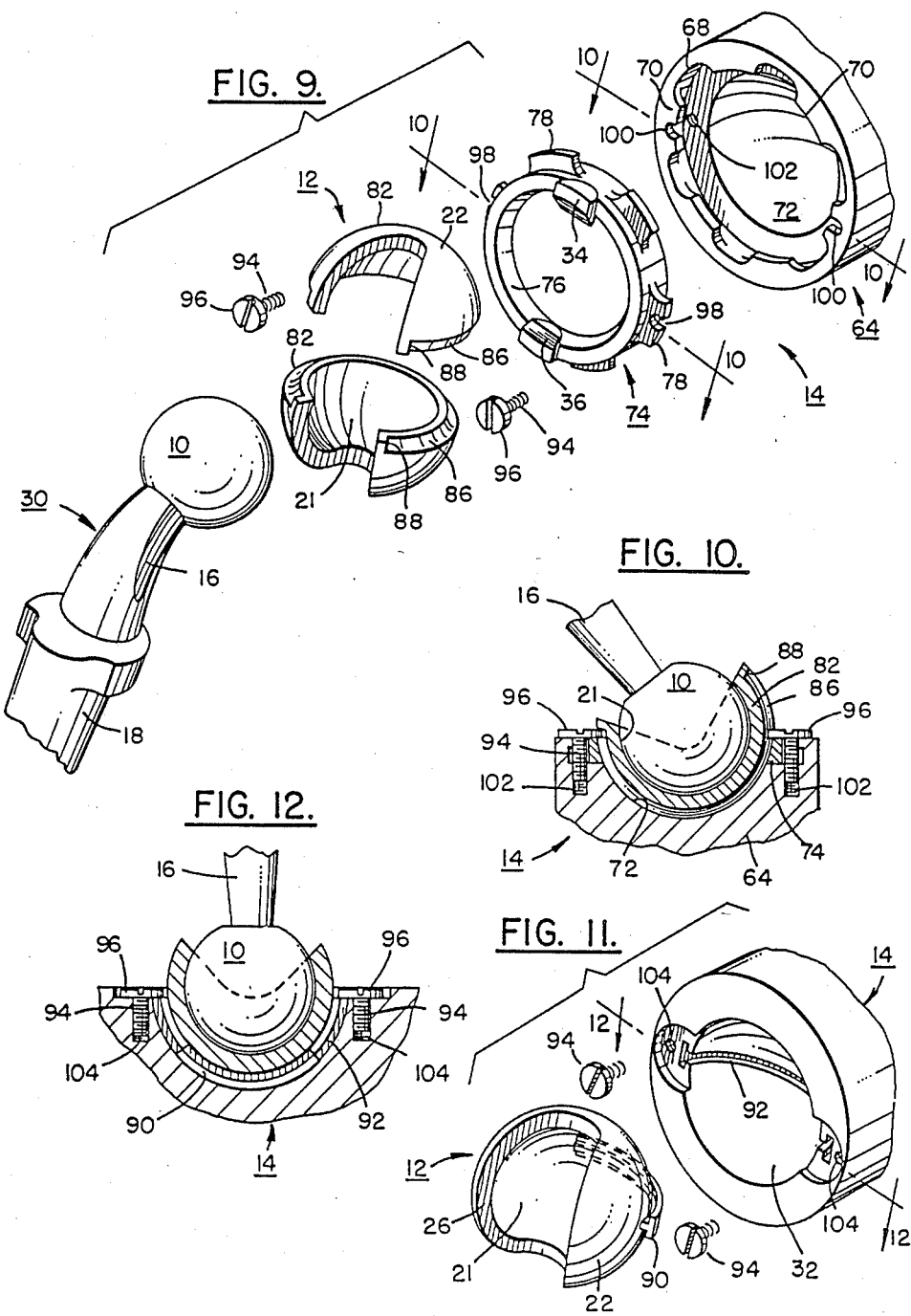

BALL AND SOCKET BEARING FOR ARTIFICIAL JOINT

This is a continuation of application Ser. No. 473,431, filed on Mar. 8, 1983, now. U.S. Pat. No. 4,642,123.

BACKGROUND OF THE INVENTION

1. Field Of The Invention

This invention relates to artificial joints and in particular to artificial joints of the ball and socket type.

2. Description Of The Prior Art

As is well known in the art, artificial hip and shoulder joints conventionally employ ball and socket articulations. The socket is embedded in one bony structure, for example, the pelvis for a hip reconstruction. The ball is attached to an arm composed of a neck and a stem or shaft, the stem or shaft being embedded in another bony structure, for example, the femur for a hip reconstruction.

Of critical importance to the success of such artificial joints is the ability to retain the ball within the socket, that is, the ability to avoid dislocations of the joint. A number of methods are known to minimize the occurrence of dislocations.

In the most common method, referred to herein as the "semi-constrained" construction, the patient's own anatomy, i.e., his muscles, tendons and ligaments, are used to retain the ball within the socket. For this construction, a hemispherical socket typically is used which allows the ball and its attached arm the maximum amount of movement without contact of the arm with the edge of the socket. The surgeon, when installing such a semi-constrained joint, must align the ball and socket as closely as possible with the patient's natural anatomy so that the patient's movements do not tend to dislocate the ball from the joint. As a general proposition, such precise alignment is easiest the first time an artificial joint is placed in a patient. Subsequent reconstructions and much more difficult to align because of deterioration of anatomical landmarks as a result of the first operation, the healing process after the operation and changes in the anatomy caused by the presence of the artificial joint.

In order to increase the inherent stability against dislocation of such semi-constrained constructions, it has become conventional to add a cylindrical portion to the hemispherical socket to make it deeper. Although the ball is not physically constrained by the socket by this adjustment, the ball does have further to travel than if just a hemisphere had been used and thus some reduction in the propensity towards dislocation is achieved. Ball and socket joints of this type generally provide an arc or range of motion of approximately 115° when a 28 mm diameter sphere is used and the socket is made a few millimeters deeper than a hemisphere. Larger ranges of motion can be obtained by keeping the size of the arm attached to the ball constant and increasing the diameter of the ball. In this way, the angular extent of the arm relative to the ball becomes smaller. In the limit, if the ball could be made progressively larger and larger, a range of motion of 180° could be achieved. In practice, however, the largest sphere in common use in artificial joints, and in particular artificial hip joints, has a diameter of 32 mm and provides a range of motion of approximately 120°. It should be noted however, that such larger sphere sizes are not universally favored because frictional torque increases with diameter.

A recent study by the Mayo clinic, which appeared in December, 1982 edition of *The Journal of Bone and Joint Surgery*, reported a dislocation frequency of 3.2% for 10,500 hip joint implant procedures using the semi-constrained construction. Such dislocations essentially make the patient immobile and can necessitate a second operation. As discussed above, the critical alignment required for the semi-constrained construction is even more difficult to achieve when a second implantation is performed. Accordingly, even higher dislocation frequencies are encountered for second and subsequent implantations.

An alternative to the semi-constrained construction is the construction wherein the ball is physically constrained within the socket. In this construction, a spherically-shaped bearing surrounds the ball and serves as the socket. The bearing is attached to a fixation element which is embedded in, for example, the patient's pelvic bone. The bearing encompasses more than one-half of the ball and thus constrains the ball and its attached arm from dislocation.

The bearing is typically made from plastic, such as ultra-high molecular weight polyethylene (UHMWPE), or metal. For plastic bearings, the ball and bearing are usually assembled by forcing the bearing over the ball. The more of the ball which is encompassed by the bearing, the greater the required assembly force, and the greater the constraining force to prevent postoperative dislocation of the joint. In addition, the more that the bearing encompasses the ball, the smaller the range of motion for the ball prior to contact of the bearing with the arm attached to the ball.

An example of a constrained artificial joint employing a plastic bearing is shown in Noiles, U.S. Pat. No. 3,996,625. As can be seen in FIG. 1 of this patent, a plastic bearing 17 fitted with a metal reinforcing band (un-numbered) extends beyond the diameter of ball 24 so as to physically constrain the ball within the bearing. The bearing itself is attached of fixation element 12. The metal reinforcing band is assembled over the lip of the opening of bearing 17 after that bearing has been forced over sphere 24. The reinforcing band increases the force required to dislocate the joint. In practice, the design shown in FIG. 1 of U.S. Pat. No. 3,996,625 has been found to provide a range of motion of approximately 85° when a sphere diameter of 28 mm is used and to resist direct dislocating forces of several hundred pounds.

For constrained constructions such as that shown in U.S. Pat. No. 3,996,625, it has been found in use that a dislocating force is created when the neck of the arm attached to the ball impinges on the rim of the bearing. Because of the leverage associated with the arm and the long bone of the patient to which it is attached, e.g., the patient's femur, the dislocating force produced when the neck contacts the rim of the bearing can be considerable. For example, a force on the order of 25 pounds applied to a patient's leg can produce a dislocating force of over several hundred pounds because of the leverages involved. This type of dislocation force can be avoided by geometrically aligning the artificial joint with the patient's anatomy so that the neck does not come in contact with the rim of the bearing during normal motion of the patient's limb. That is, the leverage based dislocation forces can be avoided in the same way as dislocations are avoided in the semi-constrained construction, i.e., through precise alignment of the artificial joint with the natural anatomy of the patient.

Unfortunately, as is apparent from the geometry of the situation, the more the socket bearing encompasses the ball, the greater the restraining force on the ball, but at the same time the less the range of motion prior to the neck impinging upon the edge of the bearing to create undesired leverage. In practice, artificial hips having the construction shown in U.S. Pat. No. 3,996,625 have been found to suffer dislocation due to the leverage effect in fewer than 0.5% of the implantations performed. This is significantly better than the 3.5% dislocation frequency reported in the Mayo clinic study discussed above, but an even lower dislocation frequency is obviously desirable.

A constrained construction using a metal socket bearing is shown in Noiles, U.S. Pat. No. Re. 28,895 (reissue of U.S. Pat. No. 3,848,272). This construction provides approximately a 90° range of motion when the sphere diameter is 28 mm. In a practical sense, the metal bearing can be said to be non-dislocatable. The force required to extract the metal sphere from the enclosing metal socket bearing is more than several thousand pounds. Accordingly, in use, rather than a metal ball dislocating from the metal socket bearing, any overly severe dislocating leverage will cause the fixation element to be disrupted from the bone in which it has been embedded.

As a general proposition, metal balls in metal socket bearings are used in only a minority of joint reconstructions because the medical profession is not in agreement that a metal sphere in a metal bearing is as biologically acceptable as a metal sphere in a UHMWPE plastic bearing, even though clinical use over 15 years has failed to show the metal to metal joint to be inferior to a metal to plastic joint.

A third type of artificial ball and socket joint, referred to as an endoprosthesis, eliminates the fixation element associated with the socket and simply uses a ball surrounded by a plastic socket bearing in a spherical metal head, which head is placed in the patient's natural socket but not secured to bone. For this construction, the ball can rotate within the bearing up to the rim of the bearing (the bearing is greater than a hemisphere so as to be retained on the ball), and then the bearing and its attached head rotates in the patient's socket. As with the semi-constrained construction, anatomical alignment is used to avoid dislocations, in this case between the metal head and the natural socket.

In view of the foregoing, it is apparent that in semi-constrained and endoprosthesis hip joints, reconstructive geometry of the prosthetic components is critical in ensuring the stability of the prosthesis against dislocation. Moreover, in ball and socket constructions which constrain the elements against dislocation, the range of motion inherent in the prosthesis is reduced and thus because of the possibility of leverage type dislocations, similar demands are placed on the surgeon to establish the geometry of the reconstruction within rather narrow limits.

Accordingly, an object of this invention is to provide a ball and socket bearing for an artificial joint which constrains the joint from dislocating and at the same time provide a range of motion which is greater than that available in the constructions of the constrained type described above.

A further object of this invention is to provide a ball and socket joint which provides the surgeon with increased latitude in geometric positioning of the prosthetic components over those ball and socket joints presently available.

A further object is to provide a prosthetic ball and socket joint of increased inherent range of motion which is readily assembled and disassembled at the surgical site.

SUMMARY OF THE INVENTION

To achieve these and other objects, the invention provides a ball and socket joint in which a ball moves within a socket bearing which is itself movable within a cup-like cavity of a fixation element. More particularly in accordance with one aspect of the invention, a ball and socket joint for implanting in the body is provided which comprises:
    a ball;
    a cup with a spherical cavity, said cup to be affixed to bone; and
    a bearing member surrounding a portion of the ball and rotatable within said spherical cavity about only one axis, said bearing member having an asymmetric opening therein, the opening having an angular extent of less than 180° in at least one plane.

In accordance with another aspect of the invention, an artificial joint of the ball and socket type for implantation in the body is provided which comprises:
    a ball;
    a bearing for forming a socket to receive the ball, the bearing having an asymmetric opening therein, the opening having an angular extent of less than 180° in a first plane;
    means for pivoting the bearing about an axis lying in a plane other than the first plane; and
    means for affixing the means for pivoting to bone.

In accordance with a further aspect of the invention, a socket for a ball and socket joint for implantation in the body is provided which comprises (1) a cup with a cavity, and (2) a bearing for receiving the ball of the ball and socket joint, said bearing being constrained to rotate within said cavity about a single axis.

In accordance with certain preferred embodiments of the invention, the asymmetric opening into the socket is less in one direction than it is at 90° to this one direction. The socket bearing is movably retained within the cup about an axis which is (1) parallel to the face of the cup and (2) in the direction of the greater opening in the socket bearing. The socket bearing is retained within the cup by two stub half round pins integral with the cup and extending part way through the wall thickness of the socket. The axes of the half round pins coincide with an axis of the spherical cup like cavity and they are also coaxial in the direction of the greater opening in the socket bearing.

When the ball and the neck of the arm of the prosthesis move in the direction of the lesser opening in the socket bearing, the total range of motion is the sum of the arc of motion which the neck can make within the bearing plus the arc of motion which the bearing can make within the cup. The cup can be a hemisphere or even less. Rotation of the ball is limited by impingement of the neck against the rim of the cup. When the diameter of the ball is approximately the 28 mm in common use, and the socket bearing wall thickness is approximately 7 mm, the inner diameter of the cup, and thus the outer diameter of the bearing, is approximately 42 mm (28 mm+7 mm+7 mm). This outer diameter for the bearing is larger than the largest diameter sphere commonly used in semi-constrained artificial hip replacements, and thus the present constrained construction achieves a greater range of motion than the semi-constrained construction, and at the same time, restrains the ball within the socket.

When the ball and the neck move in the direction of the greater opening in the socket bearing, the neck contacts the flat side of a stub half round pin, rather than the rim of the cup. To allow the neck and ball to move through the same arc in this direction, the flat sides of the pins can be contoured. With this feature, the total range of motion in all quadrants, using the above dimensions, is approximately 135°.

To summarize, in accordance with the above preferred embodiments of the invention, when motion is in the plane of the stub pins, the total motion is by movement of the ball within the bearing. When motion is at 90° to the plane of the pins (the "90° plane"), the total motion is the sum of the motion of the ball within the bearing and the motion of the bearing within the cup. In other planes, the motion of the ball within the bearing is greater than it is in the 90° plane and the motion of the bearing within the cup is less than it is in the 90° plane. In this way, the invention provides a constrained ball and socket prosthetic joint with a total range of motion significantly greater than hitherto generally available.

In connection with artificial hip joints, it is considered advantageous for the cup to be oriented so that the axis of the stub pins is inclined somewhat upward in the forward direction. In this manner almost all highly repetitive load bearing motions of the hip joint fall within the motion capability of the sphere within the socket bearing. Additional motion is furnished by movement of the bearing within the cup in such activities as crossing the legs when seated, or in significant abduction. To conveniently provide this orientation of the stub pins, in certain embodiments of the invention, the cup includes first and second portions, the first portion to be affixed to bone, the second portion having associated therewith the pin members and being moveable with respect to the first portion to provide a plurality of possible orientations for the axis of rotation of the bearing member within the spherical cavity.

In the description of the preferred embodiments which appears below, constructions are shown using both plastic and metal socket bearings. Also, three assembly and disassembly constructions are illustrated. It is to be understood, of course, that both the foregoing general description and the following detailed description are explanatory only and are not restrictive of the invention.

The accompanying drawings, which are incorporated in and constitute part of the specification, illustrate the preferred embodiments of the invention, and together with the description, serve to explain the principles of the invention.

BRIEF DESCRIPTION OF THE DRAWINGS

FIG. 5 is a cross-sectional view along lines 3—3 of FIG. 1 showing the range of motion of the ball within the socket bearing when the socket bearing moves within the cup.

FIG. 6 is an exploded view of an alternate embodiment of the invention wherein the cup includes two portions which are moveable relative to each other.

FIG. 7 is a cross-sectional view along lines 7—7 in FIG. 6 after the joint has been assembled.

FIG. 8 is a cross-sectional view along lines 8—8 in FIG. 6 after the joints has been assembled.

FIG. 9 is an alternate embodiment of the embodiment shown in FIGS. 6-8 wherein a two piece metal socket bearing is used.

FIG. 10 is a cross-sectional view along lines 10-10 in FIG. 9 after the joint has been assembled.

FIG. 11 is an exploded view showing an alternative method for rotatably retaining the socket bearing within the cup.

FIG. 12 is a cross-sectional view along lines 12—12 in FIG. 11 after the joint has been assembled.

DESCRIPTION OF THE PREFERRED EMBODIMENTS

Figure 1:
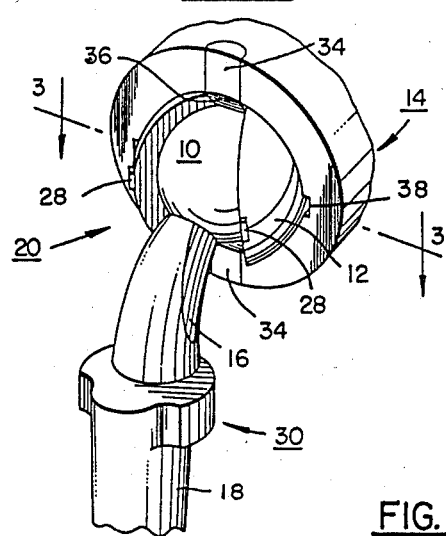
FIG. 1 is a perspective view of an artificial joint embodying the present invention.

With reference now to the drawings, wherein like reference characters designate like or corresponding parts throughout the several views, there is shown in FIG. 1 an assembly 20 of ball or sphere 10, socket bearing 12 and cup 14 for a prosthetic joint. The neck 16 of arm 30 is intermediate ball 10 and stem or shaft 18, which stem or shaft is fixed to, for example, the femur bone at the time of implant surgery.

Figure 2:
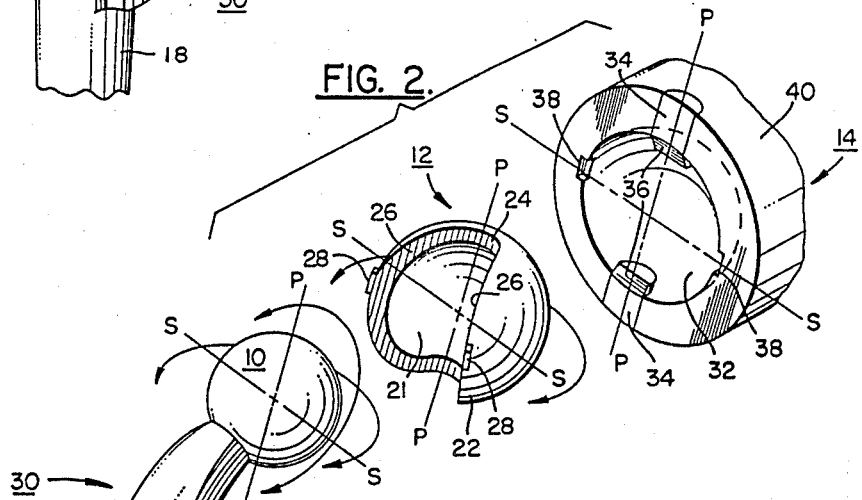
FIG. 2 is an exploded view showing the components of the joint of FIG. 1.

FIG. 2 shows in more detail socket bearing 12 of assembly 20. The preferred material for bearing 12 is ultra-high molecular weight polyethylene (UHMWPE). Inner spherical bearing surface 21 of bearing 12 is concentric with outer spherical bearing surface 22. Cylindrical surfaces 24 are coaxial with each other and with the center of spherical surfaces 21 and 22 and are tangent to surfaces 26. Small barb-shaped protuberances 28 serve a detent function described below.

In the plane passing through the lines P—P in FIG. 2, socket bearing 12 encompasses less than one half of ball 10. In the plane passing through the lines S—S, the socket bearing encompasses more than half of ball 10.

Owing to the resilience and elasticity of the plastic material of socket bearing 12, socket bearing 12 can be snapped over ball 10. The amount of interference between the equator of the ball and socket bearing 12 depends on the angular extent of the bearing's opening in the plane passing through the lines S—S in FIG. 2. The amount of interference should be such as will cause an elastic deformation of socket bearing 12 while the bearing is being assembled over the ball 10. To aid in assembly, socket bearing 12 can be heated to a non-destructive temperature (for example 70°-80° C. for UHMWPE). Plastic in general, and UHMWPE in particular, has a large coefficient of thermal expansion and such thermal expansion due to heating significantly aids in assembly.

As shown in FIG. 2, cup 14 has a hemispherical inner surface 32 and two coaxial stub half pin members 34 which are structurally integral with cup 14. The pins 34 are shown bevelled at 36. Recesses 38 are provided at the inner rim of the cup at locations 90° displaced from the pins 34. The exterior surface 40 of cup 14 is of any conventional contour for fixation in bone whether by use of cement, or without cement by means of impaction, screwing in, or by bone ingrowth into porous metal or the like. Cup 14 is normally made of metal, and it is to be understood that the metal used is to be structurally and biologically suitable for surgical implantation.

Figure 3:
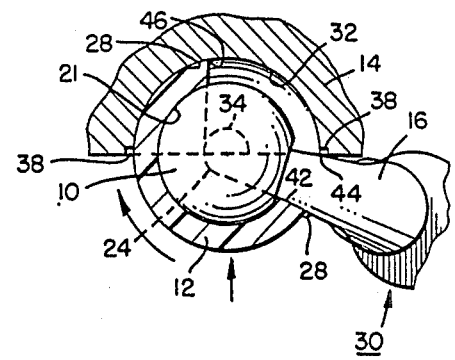
FIG. 3 is a cross-sectional view along lines 3—3 in FIG. 1 showing the ball and the socket bearing partially inserted into the cup.

A step midway in the process of assembly is schematically shown in FIG. 3 where bearing 12 has been positioned against neck 16 at 42 and the bearing 12 and arm 30 have been inserted into cup 14 with neck 16 contacting the rim of cup 14 at 44. Cylindrical surface 24 of bearing 12 engages stub pin 34 as the entering rim 46 of bearing 12 contacts inner surface 32 of cup 14. At this time the bearing 12 is pressed firmly enough into cup 14 to compress protuberance 28, allowing bearing 12 to be rotated clockwise about ball 10 and pin 34 while it is in contact with inner spherical surface 32.

When bearing 12 has been rotated sufficiently for protuberance 28 adjacent rim 46 to reach recess 38, protuberance 28 expands to resist rotation in the reverse direction and thereby resist disassembly of the ball and socket joint 20 unless a tool is inserted into recess 38 to again compress protuberance 28 as rotation in the disassembly direction is started.

The assembled joint is shown in FIG. 1, where the neck 16 of arm 30 can move through the arc from the position shown to that which is symmetrically opposite. That is, the neck of the prosthesis can move in the plane through lines P—P of FIG. 2 from a position of contact with lower stub pin 34 to contact with upper stub pin 34. When ball 10 has a diameter of 28 mm and the outer diameter of bearing 12 is 42 mm, the arc or range of motion of neck 16 is somewhat greater than 135°, depending on the design of the neck 16.

Figure 4:
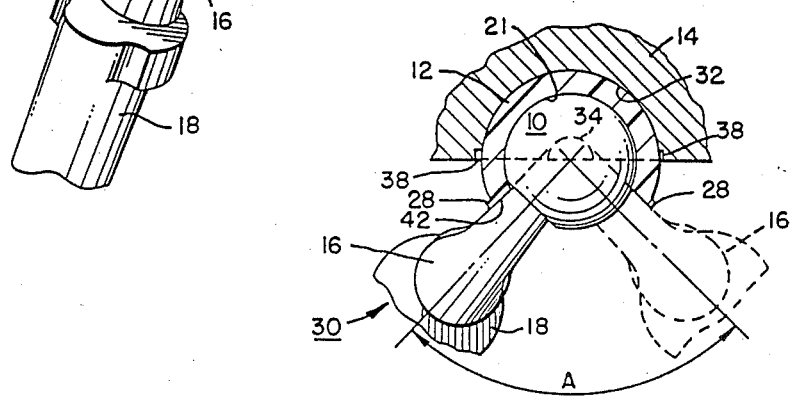
FIG. 4 is a cross-sectional view along lines 3—3 of FIG. 1 showing the range of motion of the ball within the socket bearing with the socket bearing stationary.

To achieve this same range of motion in the plane through lines S—S in FIG. 2 requires two motions. First, as shown in FIG. 4, the neck 16 and ball 10 move through the angle A by the ball 10 turning inside the socket bearing 12, at the completion of which neck 16 contacts the rim of bearing 12. Thereafter, as shown in FIG. 5, to achieve the full range of motion A', ball 10 and bearing 12 rotate in unison, at the completion of which neck 16 contacts cup 14.

Normally, until neck 16 reaches the rim of socket bearing 12, socket bearing 12 will remain stationary relative to cup 14. This is so because frictional torque is the product of friction force times the distance from the center of rotation. Given similar materials, finish and geometric accuracy. so that the coefficient of friction for ball 10 and cup 14 against bearing 12 are equal, the frictional force on inner surface 21 will be the same as that on outer surface 22 when ball 10 rotates within cup 14, because the load transmitted across the two bearing surfaces is the same. Since the radius to the outer surface 22 is the greater, the frictional torque at the outer surface will be the greater and thus motion will occur along surface 21 rather than surface 22.

For major oscillation of ball 10 and neck 16 in the plane through lines P—P in FIG. 2, the entire excursion is due to rotation of ball 10 within bearing 12. The total possible oscillation in all planes is the same, however, the contribution made by rotation of bearing 12 increases as the plane of oscillation moves from that including the lines P—P to that including the lines S—S in FIG. 2.

As described above, bearing 12 constrains ball 10 from dislocation. Further, socket bearing 12 is constrained within cup 14 by cylindrical surfaces 24 being journaled by the stub half pins 34 in all positions of bearing 12 as bearing 12 moves to allow arm 30 to move through angle A'. In the complete assembly 20, the constraint against dislocation of ball 10 by deformation of plastic bearing 12 is greater in magnitude than the force required to assemble bearing 12 over ball 10 because, in addition to the fact that the assembly operates at the body temperature of 37° C., the bearing 12 is now itself constrained against the deflection of dislocation by being captured within metal cup 14.

FIGS. 6, 7 and 8 show an alternate construction intended to (1) facilitate final assembly at the operative site, and (2) for hip joint replacements, allow the axis of stub pins 34 to be inclined somewhat upward in the forward direction. Cup 14 now includes two portions—portion 64 which is affixed in the patient's bone, and retaining ring portion 74 which carries stub pins 34 and is engageable with portion 64 at a number of locations to provide a plurality of orientations for the axis through pins 34 about which socket bearing 12 rotates. Portion 64 is shaped to accept and hold retaining ring 74 by means of bayonet spaces 68 and lugs 70. Inner spherical surface 72 is continuous with spherical surface 76 of ring 74. Ring 74 carries stub half pin members 34, has recesses 38 and bayonet lugs 78.

With this embodiment, the portion 64 of cup 14 is implanted in the patient's bone by conventional techniques. Ball 10 and bearing 12 are assembled into retaining ring 74 after stem 18 of arm 30 has been implanted in, for example, the patient's femur, the assembly procedure being the same as that described above with reference to FIG. 3 except that protuberance 28 is compressed only once it contacts the back surface of ring 74. The sub-assembly of ball 10, bearing 12 and retaining ring 74 is then inserted into portion 64 in any of the several angular positions the bayonet lug fittings will permit. A fraction of a turn in either direction will engage the lugs 78 of ring 74 under lugs 70 of portion 64. The engagement of bayonet lugs 78 and 70 is locked by conventional means, such as by one or more pins 80. Holes 79 and 81 for such locking pins can be precisely made in the cooperating parts at the time of manufacture. Although only one hole 81 is shown in FIGS. 6 and 7, a hole would normally be drilled at each bayonet space 68 so that ring 74 can be locked in place for any of its possible orientations.

For hip joints, the possibility of a number of orientations for the axis of rotation of bearing 12 is used to place that axis in an orientation which is upward in the forward direction. In this way, almost all of the highly repetitive load bearing motions of the joint will occur along or close to this axis. As discussed above, motions along or near to the axis of rotation of bearing 12 consist primarily of ball 10 moving in bearing 12, rather than bearing 12 moving in cup 14. As also discussed above, the frictional torques involved further favor movement of ball 10 in bearing 12. Accordingly, by orienting the axis of rotation of bearing 12 upward in the forward direction, most repetitive motion will occur by movement of ball 10. This is an important advantage because it means that the joint will have low friction in that friction increases with the diameter of the moving member and ball 10 has a smaller diameter than bearing 12. Put another way, by orienting the axis of rotation of the bearing 12 in the manner described above, the joint of the present invention for the great majority of motions of the patient's limb exhibits the frictional behavior of a small ball, e.g. a 28 mm ball, while providing a range of motion corresponding to a large ball, e.g. a 42 mm ball.

FIGS. 9 and 10 show another embodiment employing retaining ring 74 in which the socket bearing comprises two metal half bearings 82. A groove 86 is formed along the junction of the bearings and ends short of the edge of the bearing to form shoulders 88. Metal half bearings 82 are brought together to encompass ball 10, and the ball, half bearings, retaining ring 74 and portion 64 of cup 14 are assembled in the same manner as described above in connection with FIGS. 6–8.

Screws 94 having screw heads 96 are conveniently used both to lock lugs 70 and 78 in place and to prevent socket bearing 12 from rotating back out of retaining ring 74. Screw heads 96 ride in groove 86 and engage shoulders 88 when socket bearing 12 has been moved through its full range of motion about stub pins 34. Lugs 70 and 78 have appropriate openings 98 and 100, respectively, to receive screws 94 and allow the screws to be engaged with threaded screw holes 102. Although only two openings 100 and two threaded screw holes 102 are shown in FIGS. 9 and 10, such openings and threaded holes would normally be provided at each lug 70 so that ring 74 can be locked in place for any of its possible orientations.

As shown in FIGS. 9 and 10, and most clearly in FIG. 10, screw heads 96 for the present embodiment lie above the plane of the front face of retaining ring 74. So as to provide the same range of motion of socket bearing 12 for this embodiment as for the embodiment of FIGS. 6–8, stub pins 34 also lie above this plane, so that the axis of rotation of socket bearing 12 is in the plane of screw heads 96. For this arrangement, the motion of bearing 12, and thus arm 30, is limited by screw head 96 contacting shoulder 88, rather than by neck 16 contacting retaining ring 74.

A further embodiment of the present invention is shown in FIGS. 11 and 12. This embodiment employs means other than half stub pins 34 to define the axis of rotation of socket bearing 12 within cup 14. In particular, a dovetail arrangement is used wherein male portion 90 of the dovetail is attached to socket bearing 12 and female portion 92 of the dovetail is cut into surface 32 of cup 14. Socket bearing 12 and cup 14 are assembled in a manner similar to that shown in FIG. 3. That is, after socket bearing 12 has been placed over ball 10, the ball and socket bearing are moved into cup 14 until the center of ball 10 lies at the center of the cup's spherical cavity. Thereafter, socket bearing 12 is rotated so that male portion 90 and female portion 92 of the dovetail engage with each other. To retain socket bearing 12 within cup 14, screws 94 can be inserted into threaded holes 104 in cup 14 so as to block the outward passage of male portion 90 of the dovetail from cup 14.

Figure 13:
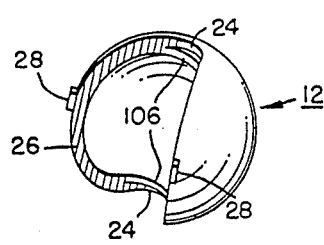
FIGS. 13 and 14 show alternative socket bearings for use with the present invention.
Figure 14:
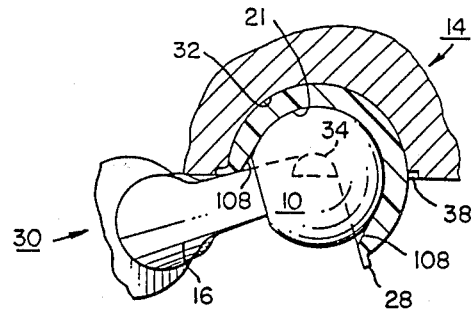

FIGS. 13 and 14 show alternate socket bearings for use with the present invention.

In FIG. 13, cylindrical surfaces 24 do not extend completely through the wall of bearing 12, but rather stop approximately half way through to leave webs 106. So as not to interfer with the range of motion of arm 30 in the plane through lines P—P (see FIG. 2), the webs only extend to the height of stub pins 34 at the end of bevels 36. The webs, although small, help restrain ball 10 within bearing 12.

FIG. 14 shows an embodiment of bearing 12 which does not physically constrain ball 10. For this embodiment, inner surface 21 of bearing 12 has a cylindrical shape 108 beyond its equator. This provides a semi-constrained type of construction having a greater depth than presently available. Such a bearing can be used with the other components of the present invention to provide the advantages, discussed above, of (1) producing a wider range of motion, e.g., on the order of 135°, and (2) providing a level of friction characteristic of a small ball for the majority of the motions of the patient's limb.

From the foregoing, it is evident that the present invention provides a constrained ball and socket joint which has a range of motion greater than that generally available in artificial joints whether of the constrained or semi-constrained type. Moreover, the present invention provides an artificial joint which can be oriented in the patient to provide low friction movement of a ball of relatively small diameter for most of the patient's repetitive activities. The limiting factor in providing the increased range of motion is the outside diameter of the bearing. Accordingly, within anatomical limits, it is advantageous for the bearing outside diameter to be as large as possible.

The increased range of motion provided by the present invention allows the patient to move his limb further than heretofore possible in constrained joints without the arm of the prosthesis impinging on the edge of the bearing. Accordingly, there is less likelihood of dislocation when plastic bearings are used or disruption of the bond between the fixation element and the bone to which it is attached when metal bearings are used. Moreover, when the range of motion of the present joint is greater than the patient can take advantage of, the surgeon is afforded greater latitude for variation in the orientation of the prosthetic components with respect to the patient's anatomy without the hazard of impingement.

Numerous modifications and variations of the present invention are possible in light of the above teachings. For example, ball 10, socket bearing 12 and retaining ring 74 can be provided to the surgeon as a unit, rather than being assembled at the surgical site. Also, metal socket bearings can be used with one piece cups, such as cup 14 shown in FIG. 1, rather than with a retaining ring as shown in FIGS. 9 and 10. It is therefore understood that within the scope of the appended claims, the invention may be practiced otherwise than as specifically described.

What is claimed is:

1. A ball and socket joint for implanting in the body comprising:
   a ball;
   first means for affixing the ball to bone including a stem portion for implantation in bone and a neck portion connecting the stem portion to the ball;
   a bearing member for receiving the ball;
   second means for affixation to bone, said means including a cavity which surrounds a portion of the bearing member, said cavity having an opening which defines a plane through which the bearing member enters the cavity;
   third means associated with the bearing member and the second means for retaining the bearing member in the cavity, said third means permitting the bearing member to be inserted into and removed from the cavity in at least one discrete initial position and permitting the bearing member to be rotated while seated in the cavity in either a clockwise or a counterclockwise direction about an axis passing through the cavity, said axis being substantially perpendicular to the plane defined by the opening of the cavity, said rotation of the bearing member permitting the bearing member to be moved from said at least one discrete initial position to any one of a plurality of intermediate positions in which the bearing member cannot be inserted or removed from the cavity, and to be moved from any one of the plurality of intermediate positions to at least one discrete final position in which the bearing member may be locked in position; and fourth means for locking the bearing member in said at least one discrete final position.

2. The ball and socket joint of claim 1 wherein the third means comprises complementary bayonet lugs and spaces.

3. Apparatus for affixing a socket bearing of an artificial ball and socket joint to bone comprising:
(a) a body to be affixed to bone which includes a cavity for receiving the socket bearing, said cavity having an opening which defines a plane through which the socket bearing enters the cavity;
(b) means for retaining the bearing in the cavity, said means permitting the bearing to be inserted into and removed from the cavity in at least one discrete initial position and permitting the bearing to be rotated while seated in the cavity in either a clockwise or counterclockwise direction about an axis passing through the cavity, said axis being substantially perpendicular to the plane defined by the opening of the cavity, said rotation of the bearing permitting the bearing to be moved from said at least one discrete initial position to any one of a plurality of intermediate positions in which the bearing cannot be inserted or removed from the cavity and to be moved from any one of the plurality of intermediate positions to at least one discrete final position in which the bearing may be locked in position; and
(c) means for locking the bearing in said at least one discrete final position.

4. The apparatus of claim 3 wherein the retaining means comprises bayonet lugs and spaces.

5. A ball and socket joint for implanting in the body comprising:
a ball;
first means for affixing the ball to bone including a stem portion for implantation in bone and a neck portion connecting the stem portion to the ball;
a bearing member for receiving the ball;
second means for affixation to bone, said means including a cavity which surrounds a portion of the bearing member, said cavity having an opening which defines a plane through which the bearing member enters the cavity;
third means associated with the bearing member and the second means for retaining the bearing member in the cavity, said third means permitting the bearing member to be inserted into and removed from the cavity in at least one discrete initial position and permitting the bearing member to be rotated while seated in the cavity about an axis passing through the cavity, said axis being substantially perpendicular to the plane defined by the opening of the cavity, said rotation of the bearing member permitting the bearing member to be moved from said at least one discrete initial position to any one of a plurality of intermediate positions in which the bearing member cannot be inserted or removed from the cavity and to be moved from any one of the plurality of intermediate positions to any one of at least two discrete final positions in which the bearing member may be locked in position; and fourth means for locking the bearing member in said any one of at least two discrete final positions.

6. The ball and socket joint of claim 5 wherein the third means comprises complementary bayonet lugs and spaces.

7. Apparatus for affixing a socket bearing member of an artificial ball and socket joint to bone comprising:
(a) a body to be affixed to bone which includes a cavity for receiving the socket bearing member, said cavity having an opening which defines a plane through which the socket bearing member enters the cavity;
(b) means for retaining the socket bearing member in the cavity, said means permitting the socket bearing member to be inserted into and removed from the cavity in at least one discrete initial position and permitting the socket bearing member to be rotated while seated in the cavity about an axis passing through the cavity, said axis being substantially perpendicular to the plane defined by the opening of the cavity, said rotation of the socket bearing member permitting the socket bearing member to be moved from said at least one discrete initial position to any one of a plurality of intermediate positions in which the socket bearing member cannot be inserted or removed from the cavity and to be moved from any one of the plurality of intermediate positions to any one of at least two discrete final positions in which the socket bearing member may be locked in position; and
(c) means for locking the socket bearing member in said any one of at least two discrete final positions.

8. The apparatus of claim 7 wherein the retaining means comprises bayonet lugs and spaces.

* * * * *